United States Patent

Hirono et al.

[11] 3,999,974
[45] Dec. 28, 1976

[54] BARBITURIC ACID DERIVATIVES

[75] Inventors: Yoshihiko Hirono, Hiratsuka; Hisao Ishikawa, Odawara; Isao Iwataki, Odawara; Mikio Sawaki, Odawara; Osami Nomura, Odawara, all of Japan

[73] Assignee: Nippon Soda Company Limited, Tokyo, Japan

[22] Filed: May 28, 1975

[21] Appl. No.: 581,625

[30] Foreign Application Priority Data

June 4, 1974   Japan ............................ 49-63210

[52] U.S. Cl. .................................. 71/92; 260/257
[51] Int. Cl.² ..................................... C07D 239/62
[58] Field of Search ...................... 260/257; 71/92

[56] References Cited
UNITED STATES PATENTS 3,828,043   8/1974   Kay .................... 260/257

Primary Examiner—Paul M. Coughlan, Jr.
Attorney, Agent, or Firm—George B. Oujevolk

[57] ABSTRACT

A compound of the formula

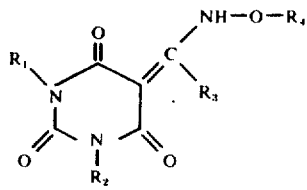

wherein $R_1$ is selected from the group consisting of hydrogen, lower alkyl, phenyl and phenyl substituted with halogen or halogenated methyl;

$R_2$ is selected from the group consisting of hydrogen, lower alkyl and lower alkenyloxy;

$R_3$ is selected from the group consisting of lower alkyl and phenyl substituted with halogen;

$R_4$ is selected from the group consisting of lower alkyl, lower alkenyl and benzyl;

or a metal salt of the compound defined herein above; is useful as herbicide.

15 Claims, No Drawings

BARBITURIC ACID DERIVATIVES

DETAILED DESCRIPTION OF THE INVENTION

This invention relates to novel compounds of barbituric acid derivatives, to a process for the preparation thereof and their uses as selective herbicide.

More particularly, this invention is directed to compositions and methods employing, as an active herbicidal ingredient, at least one compound of the formula:

wherein
- $R_1$ is selected from the group consisting of hydrogen, lower alkyl, phenyl and phenyl substituted with halogen or halogenated methyl;
- $R_2$ is selected from the group consisting of hydrogen, lower alkyl and lower alkenyloxy;
- $R_3$ is selected from the group consisting of lower alkyl and phenyl substituted with halogen;
- $R_4$ is selected from the group consisting of lower akyl, lower akenyl and benzyl;

or a metal salt of the foregoing compound.

Preferred are those compounds where $R_1$ and $R_2$ are hydrogen, $R_3$ is alkyl of 2 to 3 carbon atoms and $R_4$ is ethyl or allyl group.

Particularly preferred because of their high order of herbicidal activity are:

5-(1-allyloxyainopropylidene)barbituric acid and
5-(1-ethoxyaminopropylidene)barbituric acid.

In addition to the herbicidal effects the compounds of the present invention have both acaricidal and insecticidal activities.

The compounds of this invention can be prepared in accordance with the following equation:

wherein $R_1$, $R_2$, $R_3$ and $R_4$ are as previously defined.

The above reaction can be conducted in an inert solvent.

As an inert solvent, ether, methylalcohol, ethylalcohol, isopropylalcohol, benzene, tetrahydrofuran, chloroform, acetonitrile, dichloroethane, dichloromethane, ethyl acetate, dioxane, toluene, xylene, dimethyl formamide and dimethyl sulfoxide, etc., are used.

Reaction temperature is from room temperature to the boiling point of the employed solvent, preferably from 30° to 60° and the reaction terminates between 15 minutes and 3 hours.

After finishing the reaction, the employed solvent, if necessary, is replaced with another solvent and then, the reaction mixture is washed with an alkaline solution and water and dried, and further, solvent is distilled under reduced pressure, thereby the crude product is obtained as crystal or liquid.

The crude product can be purified by recrystallization or colum chromatography. A structural formula of the resulting purified compound can be confirmatively identified by means of an elementary analysis, NMR spectrum or IR spectrum, etc.

The sodium and potassium salts are prepared by treating a compound of formula [I] above with a sodium or potassium hydroxide in aqueous solution or an organic solvent such as methanol, ethanol or dimethylformamide. The salts are isolated by filtration or by evaporation of the resulting solution.

The calcium, barium, manganese, copper, zinc, nickel, cobalt, iron and silver salts are prepared from the sodium salt by treatment with the appropriate inorganic metal salt, e.g., calcium chloride, barium chloride, copper sulfate, zinc chloride, nickel chloride, and cobalt nitrate.

The calcium salt is also prepared by treating a compound of formula [I] above with calcium hydroxide.

With respect to the above formula [I] it is expected that the said compound has the following three chemical formulae because of tautomerism:

In order that the invention may be better understood, the following examples are given:

EXAMPLE 1

5-(1-allyloxyaminopropylidene)-barbituric acid 1.8 g of 5-propionylbarbituric acid was dissolved in 30 ml of dimethylformamide and after the temperature of said solution was raised to 40° C, 1.5 g of allyloxyamine was added to it and the resulting solution was stirred at 40° C during 3 hours and then, about 10 ml of said dimethylformamide was distilled off and after 50 ml of ethanol was added to it, the separated crystal was filtered and recrystallized from ethanol and thereby, 2.1 g of the desired compound was obtained as a white columns.

m.p. [172°–173]° C decomposition;
Yield rate: 72%

EXAMPLE 2

5-(1-ethoxyaminoethylidene)-1,3-dimethylbarbituric acid 1.5 g of 5-acetyl-1,3-dimethylbarbituric acid was dissolved in 50 ml of ethanol and 1.5 ml of ethoxyamine was added to it. After the resulting solution was stirred at 40° C during 2 hours, it was allowed to stand at a room temperature. The separated white plates were filtered and recrystallized from ethanol, and thereby 1.4 g of the desired compound was obtained.

m.p. [143°–145]° C;
Yield rate: 58%

EXAMPLE 3

5-(1-allyloxyaminopropylidene)-1,3-dimethylbarbituric acid 2.1 g of 1,3-dimethyl-5-propionyl was dissolved in 30 ml of ethanol and 1 g of allyloxyamine was added to it. After stirring at a room temperature during 2 hours, said ethanol was distilled off and white crystals separated. The separated crystals recrystallized from methanol and thereby 2.3 g of the desired compound was obtained as white columns.

m.p. [56°–58]° C;
Yield rate: 86%

EXAMPLE 4

5-(1-allyloxyaminobutylidene)-1,3-dimethylbarbituric acid 2.3 g of 5-butyryl-1,3-dimethylbarbituric acid was dissolved in 30 ml of ethanol and 1 g of allyloxyamine was added to it at a temperature of 30° C. After stirring during 2 hours, said ethanol was distilled off and thereby 2.6 g of white crystals was separated. The purified compound was obtained as needles by recrystallization from methanol.

m.p. [59°–60]° C;
Yield rate: 93%

In addition to the above mentioned compounds described in the preceding example, some typical compounds of the present invention are listed in Table 1.

Table 1

| Compound No. | Chemical Name | Physical Constant* |
|---|---|---|
| 1 | 5-(1-allyloxyaminopropylidene)barbituric acid | m.p. 172–173° C (d.) |
| 2 | 5-(1-ethoxyaminoethylidene)barbituric acid | m.p. 204–206° C (d.) |
| 3 | 5-(1-ethoxyaminoethylidene)-1,1-dimethylbarbituric acid | m.p. 143–145° C (d.) |
| 4 | 5-(1-ethoxyaminopropylidene)barbituric acid | m.p. 184–186° C (d.) |
| 5 | 5-(1-ethoxyamino-2-methylpropylidene)-1,3-dimethylbarbituric acid | m.p. 191–192° C (d.) |
| 6 | 5-(1-ethoxyaminopropylidene)-1,3-dimethylbarbituric acid | m.p. 76–78° C (d.) |
| 7 | 5-(1-allyloxyaminopropylidene)-1,3-dimethylbarbituric acid | m.p. 56–58° C |
| 8 | 5-(1-allyloxyaminobutylidene)-1,3-dimethylbarbituric acid | m.p. 59–60° C |
| 9 | 5-(1-allyloxyaminoethylidene)-1-ethyl-3-(m-trifluoromethylphenyl)barbituric acid | m.p. 82–83° C |
| 10 | 5-(α-ethoxyamino-p-chlorobenzylidene)-1,3-dimethylbarbituric acid | m.p. 96–99° C |
| 11 | 1-t-butyl-3-methyl-5-(1-ethoxyaminopropylidene)barbituric acid | $n_D^{20}$ 1.5232 |
| 12 | 1-allyloxy-3-phenyl-5-(1-ethoxyaminopropylidene)barbituric acid | $n_D^{22}$ 1.5592 |
| 13 | 5-(1-ethoxyaminohexylidene)barbituric acid | m.p. 190–191° C (d.) |
| 14 | 5-(1-benzyloxyaminohexylidene)barbituric acid | m.p. 167–168° C |
| 15 | 5-(1-ethoxyaminopropylidene)-1-methylbarbituric acid | m.p. 129–131° C |
| 16 | 5-(1-allyloxyaminobutylidene)barbituric acid | m.p. 184–185° C |
| 17 | 5-(1-ethoxyaminobutylidene)barbituric acid | m.p. 198–199° C (d.) |
| 18 | 5-(1-allyloxyaminobutylidene)-1-methylbarbituric acid | m.p. 133–134° C |
| 19 | 5-(1-allyloxyaminopropylidene)-1-methylbarbituric acid | m.p. 130–131° C |
| 20 | 5-(1-allyloxyaminopropylidene)-1-phenylbarbituric acid | m.p. 150–152° C |
| 21 | 5-(1-ethoxyaminopropylidene)-1-phenylbarbituric acid | m.p. 189–190° C |
| 22 | 1-methyl-3-(3,4-dichlorophenyl)-5-(1-ethoxyaminopropylidene)barbituric acid | m.p. 99–102° C |
| 23 | 1-methyl-3-(3,4-dichlorophenyl)-5-(1-allyloxyaminopropylidene)barbituric acid | m.p. 123.–135° C |

Table 1-continued

| Compound No. | Chemical Name | Physical Constant* |
|---|---|---|
| 24 | Sodium salt of 5-(1-allyloxyamino-propylidene)barbitric acid | >m.p. 270° C |
| 25 | Calcium salt of 5-(1-allyloxyamino-propylidene)barbituric acid | >m.p. 270° C |
| 26 | Copper salt of 5-(1-allyloxyamino-propylidene)barbituric acid | >m.p. 270° C |
| 27 | Potassium salt of 5-(1-allyloxyamino-butylidene)barbituric acid | m.p. 263–264° C (d.) |
| 28 | Sodium salt of 5-(1-ethoxyaminobutylidene)barbituric acid | m.p. about 250° C (d.) |
| 29 | Calcium salt of 5-(1-allyloxyamino-butylidene)barbituric acid | >m.p. 270°C |
| 30 | Copper salt of 5-(1-allyloxyamino-butylidene)barbituric acid | m.p. 198–199° C (d.) |

*m.p. melting point
Sodium
(d.) decomposition 123.5–125° C24
$n_D$ refractive index Hereinafter, the compounds of this invention are represented by Compound No. in Table 1.

As mentioned previously, it has been found that the compounds of the invention possess superior herbicidal activity. The paragraphs which follow described in more detail the utility of this invention.

The compounds of the invention are particularly effective in the control of grass weeds such as annual bluegrass (*Poa annua* L.), water foxtail (*Alopecurus aequalis* Sobol), large crabgrass (*Digitaria adscendens* Henr.), green foxtail (*Seturia viridis* Beauv), wild oat (*Avena fatua* L) etc. and they hardly injure broad leaf crops such as adzuki bean (*Phaseolus angularis* W. F. Wight) and soy bean (*Glycine max* Merrill) and sugar beets (*Beta vulgaris* L.) which easily suffer phyto-toxicity. Namely, the compound of the invention are the selective herbicide.

In the case of foliar treatment using the compounds of the present invention, even the same amount of chemical which completely kills barnyard grass of grass weeds gives no damages to broadleaf plants such as radish (*Raphanus sativus* L.), soy bean, garden pea (*Pisum sativum* L.), spinach (*Spinacia oleracea* L.) sugar beets and carrot (*Daucus carota* L.) at all, and in case of soil treatment before germination, even the same amount of chemicals which prevents large crabgrass germinating gives no damages to seeds of broad leaf plants at all.

As mentioned above, a security to the broadleaf crop against phytotoxicity of the herbicide is extremely high and as to its application, in other words, its applicable time, its applying location and its applying concentration, it has a very broad extent and it can be used in the wider extent.

It is another advantage of the present invention that a residual toxicity in the soil or the plant and an acute toxicity for warm blooded animals and fish are not feared because the said compounds can be used with a low chemical concentration.

The compound of this invention can be applied directly to the soil as preemergence treatment or to plant foliage, as post-emergence treatment, or they can be mixed intimately with the soil, preferably post-emergence treatment to plant foliage, and may be applied to soil or plant foliar at rates of 50–1000 g per 10 are, preferably 100–400 g per 10 are, more preferably about 200 g per 10 are.

The method of the present invention comprehends the employment of a liquid or solid composition containing one or more of the present compounds as an active ingredient.

The active ingredient of this invention may be formulated by mixing with suitable carriers in a form generally used in agricultural chemicals such as wettable powder, emulsifiable concentrate, dust formulation, granular formulation, water soluble powder and aerosol. As solid carriers, bentonite, diatomaceous earth, apatite, gypsum, talc, pyrophyllite, vermiculite, clay and others are used. As liquid carriers, kerosene, mineral oil, petroleum, solvent naphtha, benzene, xylene, cyclohexane, cyclohexanone, dimethylformamide, alcohol, acetone, and others are used. Sometimes surface active agent is added in order to give a homogeneous and stable formulation.

The compounds of this invention also can be applied admixed with other chemicals which are used in agronomic and horticultural management and are compatible with the compounds of this invention. Such chemicals can be, but are not restricted to, the classes of chemicals commonly known as plant nutrients, fertilizers, insecticides, acaricides, fungicides, herbicides and nematocides.

As for known herbicides it is recommended that the compound of the present invention is applied admixed with urea derivatives such as 3(3,4-dichlorophenyl)-1-methoxy-1-methyl urea, or N-(3,4-dichlorophenyl)N',N'-dimethylurea, triazine derivatives such as 2-chloro-4-ethylamino-6-isopropylamino-s-triazine, or 2-chloro-4,6-bis(ethylamino)-s-triazine and amide derivatives such as N-1-naphthyl-phthalamic acid.

The concentrations of the active ingredients in the herbicidal composition of this invention vary according to type of formulation, and they are, for example, used in a range of 5–80 weight percent, preferably 10–60 weight percent, in wettable powder, 5–70 weight percent, preferably 20–60 weight percent, in emulsifiable concentrates, and 0.5–30 weight percent, preferably 1–10 weight percent in dust formulation.

Thus, a wettable powder or an emulsifiable concentrate produced thereto is diluted with water to a specified concentration and thereby, it is used as a liquid suspension or a liquid emulsion for treating soils or plant foliars. Further, a dust formulaton is directly used for the soil treatment or the foliar treatment.

The non-limiting examples for the herbicidal, acaricidal and insecticidal compositions are illustrated as follows:

EXAMPLE 5

Wettable Powder

| | Parts by weight |
|---|---|
| Compound 1 | 20 |
| Diatomaceous earth | 35 |
| Sodium alkylsulfate | 6 |
| Talc | 35 |
| White carbon | 4 |

These are mixed homogeneously and reduced to fine particles. Consequently, wettable powder containing 20% of active ingredient is obtained. In practical use, it is diluted to a certain concentration with water and is sprayed as a supension.

EXAMPLE 6

Emulsifiable Concentrate

| | Parts by weight |
|---|---|
| Compound 2 | 40 |
| Xylene | 33 |
| Dimethylformamide | 15 |
| Polyoxyethylene phenylether | 12 |

These are mixed and dissolved.
Consequently, emulsifiable concentrate containing 40% of the active ingredient is obtained. In practical use, it is diluted to certain concentration with water and then is sprayed an emulsion.

EXAMPLE 7

Dust Formulation

| | Parts by weight |
|---|---|
| Compound 3 | 5 |
| Talc | 38.5 |
| Bentonite | 10 |
| Clay | 38.5 |
| Sodium alkylsulfate | 8 |

These are mixed homogeneously and reduced to fine particles. Fine particles are made into granules having the diameter in the range of 0.5–1.0 mm by granulator.

Consequently, dust formulation containing 5% of the active ingredient is obtained. In practical use it is directly applied.

The superior herbicidal, acaricidal and insecticidal effect of the novel compounds of this invention is clearly illustrated by the following test.

Test 1. Pre-emergence treatment (soil treatment in paddy condition)

About 60 seeds of barnyard grass were planted in a pot having 60 square centimeters and covered slightly with soil. Water was poured into the pot until the surface of soil became wet.

10 ml of an aqueous emulsion prepared by diluting an emulsifiable concentrate with water to a specified concentration was sprayed on the pot. The pots were kept in a green house and water was added to the pots daily in order to keep the water level. Two weeks after spraying, the degrees of damage to the plant were observed and estimated by the values of 0–5 which have the following meanings:

0: no effect
1: partial plant slightly injured
2: plant slightly injured
3: plant moderately injured
4: plant severely injured
5: plant completely killed or no germination The results were shown in Table 2.

Table 2

| Test Compound No. | Application rate (g/19 ares) | | | |
|---|---|---|---|---|
| | 120 | 60 | 30 | 15 |
| 1 | 5 | 5 | 5 | 3 |
| 2 | 5 | 3 | 1 | 0 |
| 3 | 4 | 2 | 0 | 0 |
| 4 | 5 | 5 | 5 | 3 |
| 6 | 5 | 5 | 2 | 0 |
| 7 | 5 | 3 | 1 | 0 |
| 8 | 5 | 4 | 1 | 0 |
| Comparative compound * | 3 | 2 | 0 | 0 |
| Untreated | 0 | | | |

\* Japanese patent publication No. 46-16916

Test 2. Pre-emergence treatment

Seeds of large crab-grass were planted in a pot having 100 square centimeters. 5 ml of an aqueous emulsion prepared by diluting an emulsifiable concentrate with water to a specified concentration was sprayed on the surface of the soil before emergence. The pots were kept in a green house. 21 days after spraying, the degrees of damage to the test plants were observed and estimated by the value of 0–5 which have the same meanings as those of Test 1.

The results were shown in Table 3.

Table 3

| Test Compound No. | Application rate (g/10 ares) | | | |
|---|---|---|---|---|
| | 250 | 125 | 62.5 | 31.3 |
| 1 | 5 | 4 | 3 | 2 |

Table 3-continued

| Test Compound No. | Application rate (g/10 ares) | | | |
|---|---|---|---|---|
| | 250 | 125 | 62.5 | 31.3 |
| 2 | 4 | 3 | 1 | 0 |
| 4 | 5 | 4 | 3 | 2 |
| 6 | 4 | 2 | 0 | 0 |
| 7 | 4 | 3 | 1 | 0 |
| Untreated | | 0 | | |
| Comparative compound | 4 | 1 | 0 | 0 |

Test 3. Post-emergence treatment (foliar treatment)

Seeds of large crab-grass was planted in a pot having 100 square centimeters. When plants became 2-4 leaves stage, an aqueous emulsion prepared by diluting an emulsifiable concentrate with water to a specified concentration was sprayed on the foliar of the test plant at a rate of 100 liters per 10 are. The plants were kept in a green house.

21 days after spraying, the degrees of damage to the test plant were observed and estimated by the value of 0-5 which have the same meanings as those of Test 1. The results were shown in Table 4.

Table 4

| Test Compound No. | Application rate (g/10 ares) | | |
|---|---|---|---|
| | 100 | 50 | 25 |
| 1 | 5 | 5 | 4 |
| 2 | 4 | 2 | 0 |
| 3 | 4 | 2 | 0 |
| 4 | 5 | 5 | 4 |
| 6 | 4 | 2 | 0 |
| 7 | 5 | 4 | 2 |
| 8 | 5 | 4 | 2 |
| Comparative compound | 3 | 2 | 0 |
| | 3 | 1 | 0 |

Test 4. Test for Control of Tetranychus mite

About 30 adult female mites of Tetranychus mite (*Tetranychus desertorum*) laid on main leaves of the potted kidney bean plants grown 7 to 10 days stage after sprouting. One day later, the wounded mites were removed from the plants. The compounds to be tested were sprayed on the plants as water suspension containing 0.05% of the compound prepared by diluting an emulsifiable concentrate with water. After 3 days from spraying, adult mortality was counted, and then the surviving adult mites were removed. The viability of eggs deposited during this period was examined after 11 days from spraying.

Adult mortality and efficacy were calculated by the following:

Adult mortality (%): $[(a - b)/a] \times 100$
a: number of living mites in untreated plots
b: number of surviving mites in treated plots
Efficacy (%): $[(a' - b')/a'] \times 100$
a': number of eggs deposited
b': number of hatched eggs But, rating of adult mortality and efficacy was recorded as follows:

| Adult mortality or Efficacy | Rating |
|---|---|
| 100% | +++ |
| 80 - 99% | ++ |
| 50 - 79% | + |
| 0 - 49% | − |

The results are shown in Table 5.

Table 5

| Test Compound No. | Adult mortality after 3 days | Efficacy after 11 days |
|---|---|---|
| 1 | − | ++ |
| 6 | + | − |
| 7 | + | + |
| 8 | +++ | + |
| 9 | − | + |
| 10 | − | + |
| 11 | +++ | + |
| Tetradifon* | − | +++ |

*3,4,5,4'-tetrachlorodiphenyl sulfone.

Test 5. Insecticidal activity against Fly

A feed containing 49% of powder milk, 49% of sugar and 1% of the test compound and water are put into a cage where 20 pieces of each male and female adults of house fly (*Musca domestica* Linne) are living.

Said cage is kept at a temperature of 25° C and at a humidity of 65%.

After 5 days, dead flies are counted and mortality (%) is calculated.

The results are shown in Table 6.

Table 6

| Test Compound No. | Mortality (%) |
|---|---|
| 6 | 100 |
| 7 | 100 |
| 8 | 90 |
| 9 | 78 |

Table 6-continued

| Test Compound No. | Mortality (%) |
|---|---|
| Chlorodimeform* | 10 |

*N'-(4-chloro-0-totyl)-N,N-dimethyl-formamidine

Test 6. Insecticidal activity against smaller brown planthopper

Young rice-plants are dipped during 30 seconds in an aqueous emulsion containing 0.05% of test compound prepared by diluting an emulsifiable concentrate with water and air dried. Above young rice-plants are put into a test-tube where smaller brown planthopper (*Laodelphax striatellus Fallen*) are living and said test-tube is covered with lint. Above test-tube is kept at a temperature of 25° C and at a humidity of 65%.

After 48 hours, dead smaller brown planthoppers are counted and mortality (%) is calculated.

The results are shown in Table 7.

Table 7

| Test Compound No. | Mortality (%) |
|---|---|
| 4 | 90 |
| 8 | 70 |
| Chlorodimeform* | 40 |

*N'-(4-chloro-0-totyl)-N,N-dimethyl-formamidine

What is claimed is:

1. A compound of the formula

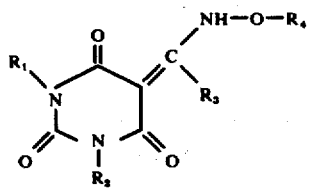

wherein
$R_1$ is selected from the group consisting of hydrogen, alkyl of 1 to 4 carbon atoms, phenyl and phenyl substituted with chlorine or trifluoromethyl;
$R_2$ is selected from the group consisting of hydrogen, alkyl of 1 to 2 carbon atoms and allyloxy;
$R_3$ is selected from the group consisting of alkyl of 1 to 5 carbon atoms and phenyl substituted with chlorine;
$R_4$ is selected from the group consisting of alkyl of 1 to 3 carbon atoms, allyl and benzyl;
or a metal salt of the foregoing compound, wherein metal is selected from the group consisting of sodium, potassium, calcium and copper.

2. A compound of the formula

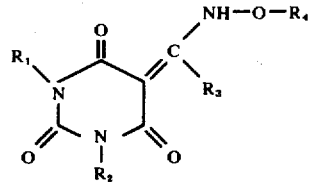

wherein
$R_1$ and $R_2$ are hydrogen,
$R_3$ is alkyl of 2 to 3 carbon atoms and
$R_4$ is selected from the group consisting of ethyl and allyl.

3. 5-(1-ethoxyaminopropylidene)barbituric acid.
4. 5-(1-allyloxyaminopropylidene)barbituric acid.
5. The sodium, potassium, calcium and copper salts of a compound of the formula

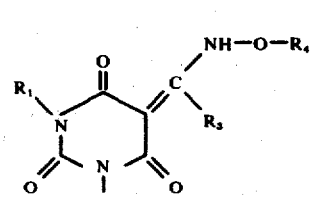

wherein $R_1$ and $R_2$ are hydrogen,
$R_3$ is alkyl of 2 to 3 carbon atoms and
$R_4$ is selected from the group consisting of ethyl and allyl.

6. A herbicidal composition containing an inert carrier and an effective amount of a compound of claim 1.
7. A herbicidal composition containing an inert carrier and an effective amount of a compound of claim 2.
8. A herbicidal composition containing an inert carrier and an effective amount of a compound of claim 3.
9. A herbicidal composition containing a inert carrier and an effective amount of a compound of claim 4.
10. A herbicidal composition containing an inert carrier and an effective amount of a cmpound of claim 5.
11. A method for the control of weeds comprising applying a compound of claim 1 in an amount sufficient to excert herbicidal action to a locus to be protected.
12. A method for the control of weeds comprising applying a compound of claim 2 in an amount sufficient to excert herbicidal action to a locus to be protected.
13. A method for the control of weeds comprising applying a compound of claim 3 in an amount sufficient to excert herbicidal action to a locus to be protected.
14. A method for the control of weeds comprising applying a compound of claim 4 in an amount sufficient to excert herbicidal action to a locus to be protected.
15. A method for the control of weeds comprising applying a compound of claim 5 in an amount sufficient to excert herbicidal action to a locus to be protected.

* * * * *